US005627277A

United States Patent [19]
Cohen et al.

[11] Patent Number: 5,627,277
[45] Date of Patent: *May 6, 1997

[54] METHOD FOR ANALYZING OLIGONUCLEOTIDE ANALOGS

[75] Inventors: Aharon S. Cohen, Brookline; Andre Bourque, Marlboro; Maria Vilenchik, Waban, all of Mass.

[73] Assignee: Hybridon, Inc., Worcester, Mass.

[*] Notice: The term of this patent shall not extend beyond the expiration date of Pat. No. 5,420,265.

[21] Appl. No.: 178,660

[22] Filed: Jan. 7, 1994

Related U.S. Application Data

[63] Continuation-in-part of Ser. No. 32,856, Mar. 16, 1993, which is a continuation-in-part of Ser. No. 991,466, Dec. 16, 1992, Pat. No. 5,420,265.

[51] Int. Cl.⁶ .......................... C07H 21/00; G01N 27/26; A61K 48/00; C12P 19/34
[52] U.S. Cl. .......................... 536/25.4; 204/455; 435/6; 435/91.2; 435/91.1; 514/44
[58] Field of Search .......................... 204/182.8; 536/93, 536/25.4; 435/6, 91.1, 91.2; 514/44

[56] References Cited

U.S. PATENT DOCUMENTS

| | | | |
|---|---|---|---|
| 4,816,571 | 3/1989 | Andrus et al. | 536/25.3 |
| 4,865,706 | 9/1989 | Karger et al. | 427/8 |
| 4,865,707 | 9/1989 | Karger et al. | 204/453 |
| 4,965,349 | 10/1990 | Woo et al. | 536/25.3 |
| 5,047,524 | 9/1991 | Andrus et al. | 536/25.31 |
| 5,112,460 | 5/1992 | Karger et al. | 204/455 |
| 5,262,530 | 11/1993 | Andrus et al. | 536/25.31 |
| 5,338,428 | 8/1994 | Zewert et al. | 204/182.8 |
| 5,420,265 | 5/1995 | Cohen | 536/25.4 |

FOREIGN PATENT DOCUMENTS

0497448A1  5/1992  European Pat. Off. .

OTHER PUBLICATIONS

Heiger et al. "Separation of DNA Restriction Fragments by High Performance Capillary Electrophoresis with Low and Zero Crosslinked Polyacrylamidde Using Continuous and Pulsed Electric Fiels" J. of Chromatography 516: 33–48, 1990.

Ruiz–Martinez et al. "DNA Sequencing by Capillary Gel Electrophoresis with Replaceable Linear Polyacrylamide and Laser Induced Fluorescence Detection" Anal. Chem. 65: 2851–2858, Oct. 15, 1993.

Pentoney et al. "A Single Fluor Approach to DNA Sequence Determination Using High Performance Capillary Electrophoresis" Electrophoresis 13: 467–474, 1992.

Hjerten (1967) Chromatogr. Rev. 9:112–213 Found in 08032856.

Burgers et al. (1979) Biochemistry 18:592–596.
Edge et al. (1981) Nature 292:756–762.
Stec et al. (1985) J. Chromatogr. 326:263–280.
Froehler (1986) Tetrahedron Lett. 27:5575–5578.
Murakami et al. (1986) Biochem. 24:4041–4046.
Agrawal et al. (1987) Tetrahedron Lett. 28:3539–3542.
Agrawal et al. (1988) Proc. Natl. Acad. Sci. (USA) 85:7079–7083.
Andrus et al. (1988) Tetrahedron Lett. 29:861–864.
Cohen et al. (1988) Proc. Natl. Acad. Sci. (USA) 85:9660–9664.
Sarin et al. (1988) Proc. Natl. Acad. Sci. (USA) 85:7448–7451.
Agrawal et al. (1989) Nucleosides and Nucleotides 8:819–823.
Agrawal et al. (1989) Proc. Natl. Acad. Sci. (USA) 86:7790–7794.
Agrawal et al. (1990) J. Chromatog. 509:396–399.
Agrawal et al. (1990) Nucleic Acids Res. (USA) 19:5419–5420.
Bigelow et al. (1990) J. Chromatog. 553:133–140.
Heiger et al. (1990) J. Chromatogr. 516:33–48.
Brumley et al. (1991) Nucleic Acids. Res. 19:4121–4126.
Agrawal et al. (1992) Trends in Biotechnol. 10:152–158.
Bergot et al. (1992) J. Chromatog. 559:35–42.
Rocheleau et al. (1992) Electrophoresis 13:484–486.
Metelev et al. (1992) Analyt. Biochem. 200:342–346.
Cohen et al. (1993) J. Chromatogr. 638:293–301.
Cohen et al. (1993) Trends in Analytical Chem. 12:195–202.
Copy of International Search Report (dated May. 19, 1995).

Primary Examiner—W. Gary Jones
Assistant Examiner—Dianne Rees
Attorney, Agent, or Firm—Hale and Dorr

[57] ABSTRACT

Disclosed is a substrate useful for separating unmodified and modified mononucleotides and oligonucleotides. The substrate includes at least 12% (weight:volume) polymer in at least 5M urea and at least 32% (volume:volume) organic solvent, the organic solvent being a chemically stable liquid at room temperature and having a dielectric constant of at least 20. Also provided is a method of separating unmodified and modified mononucleotides and/or oligonucleotides utilizing this substrate.

25 Claims, 12 Drawing Sheets

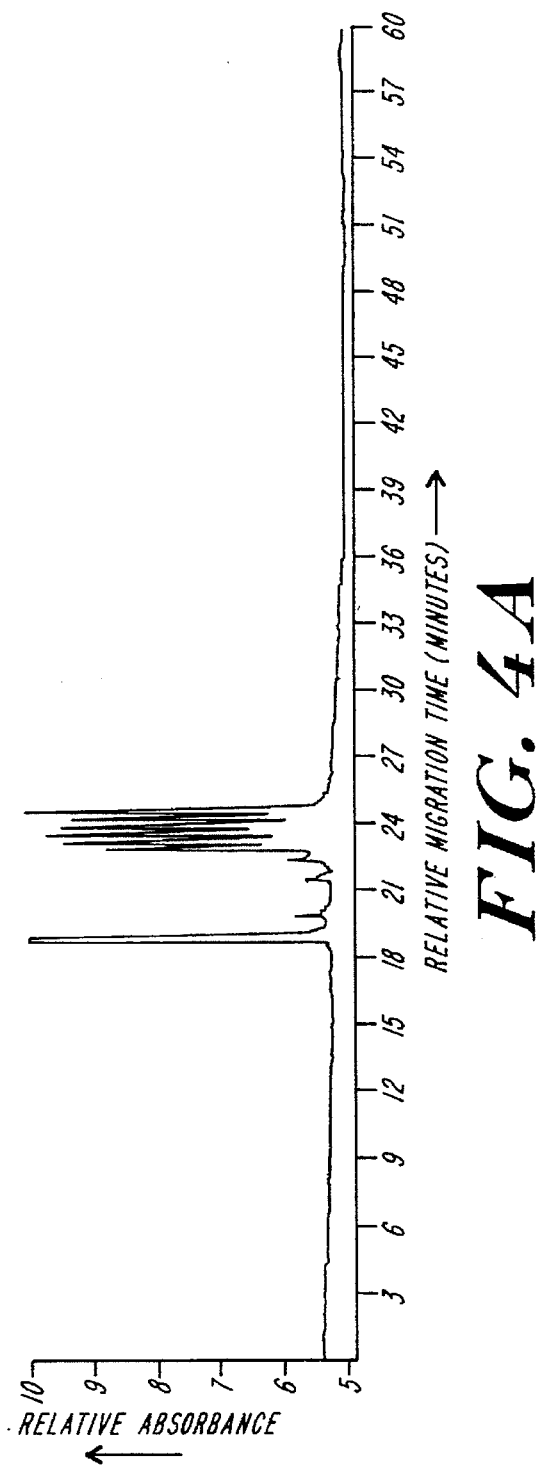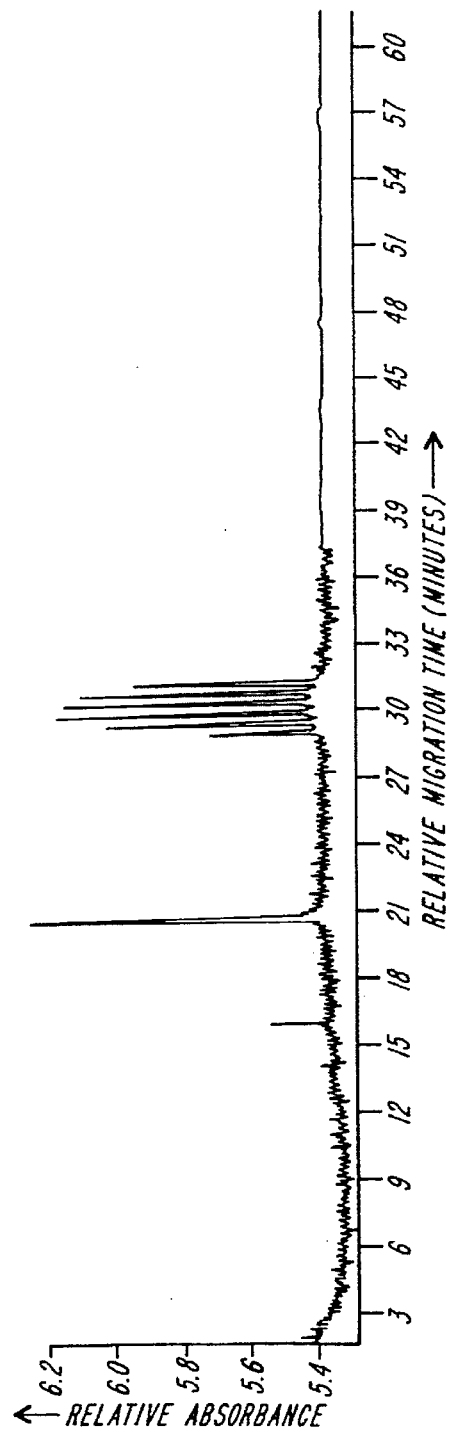

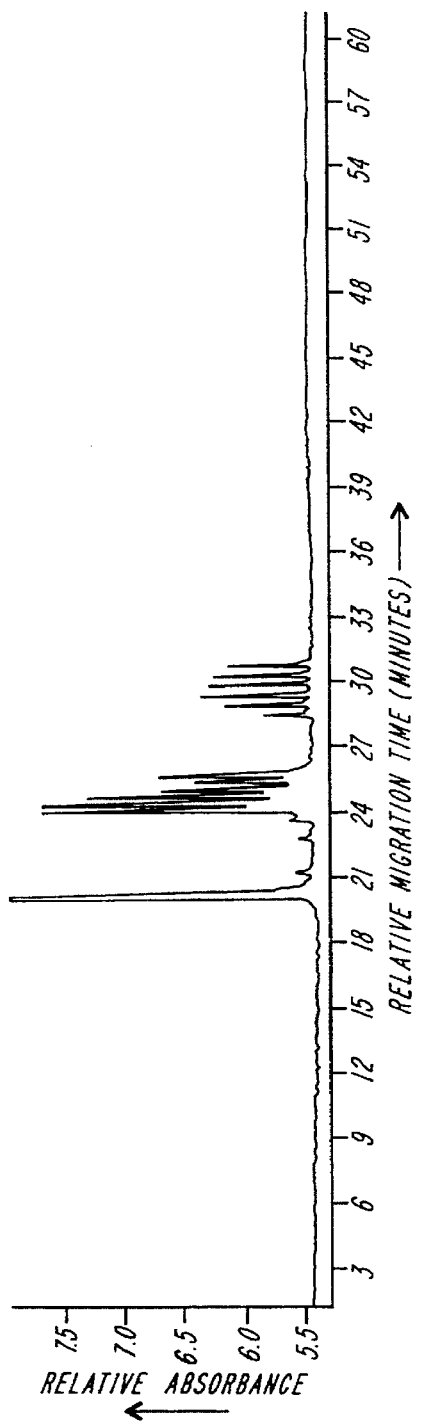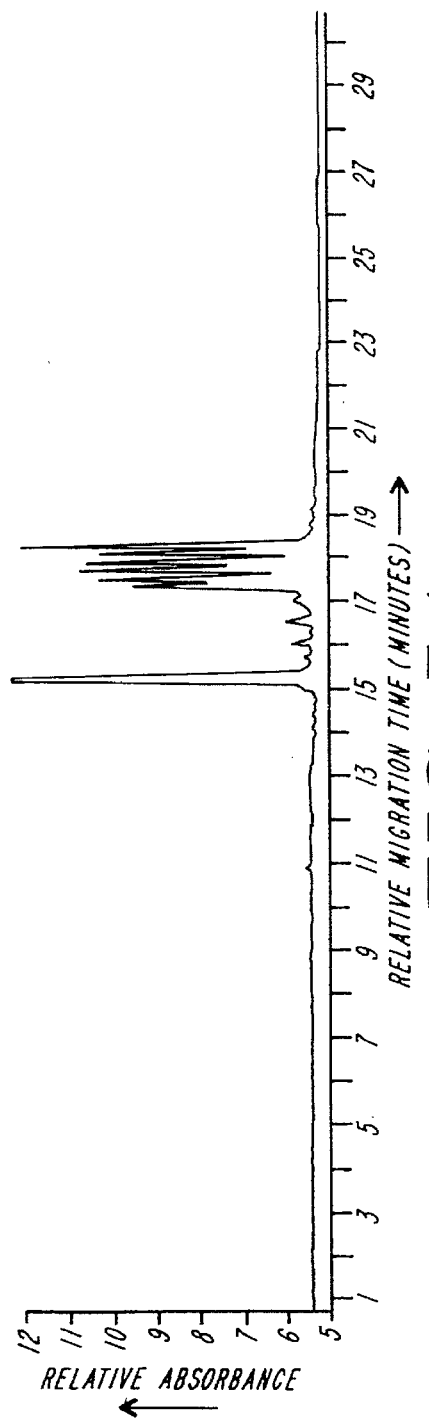

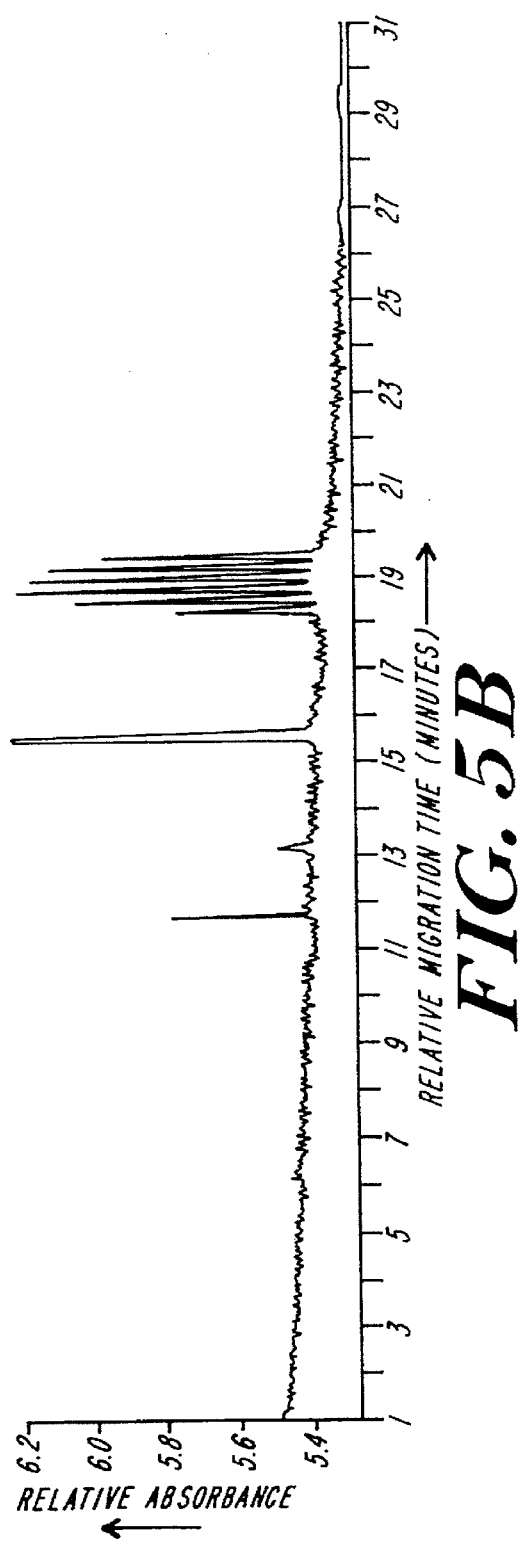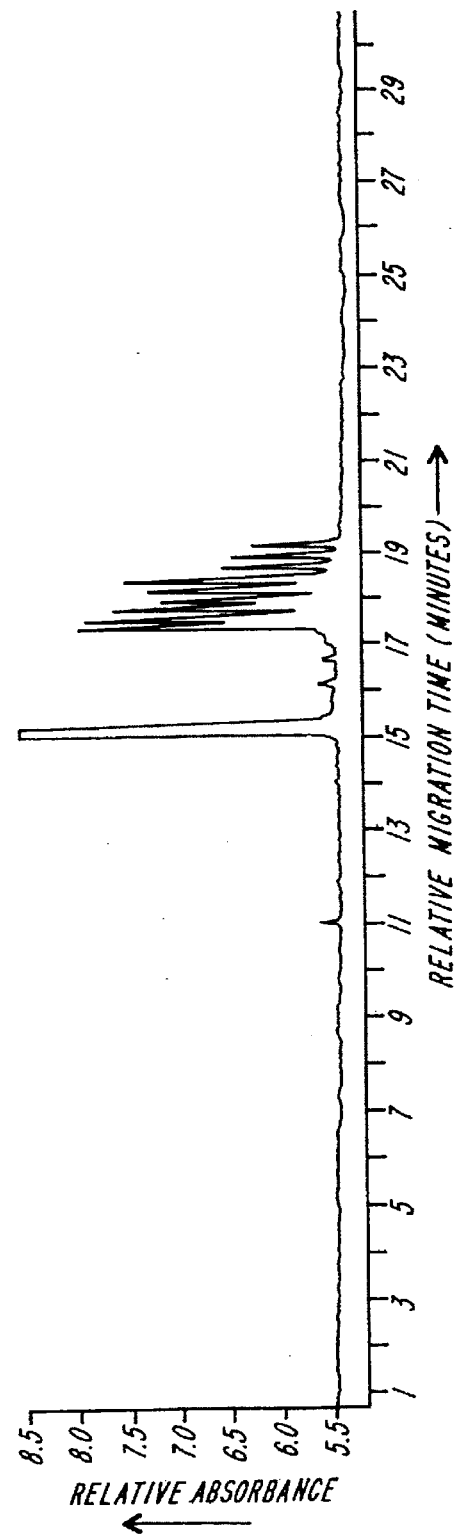

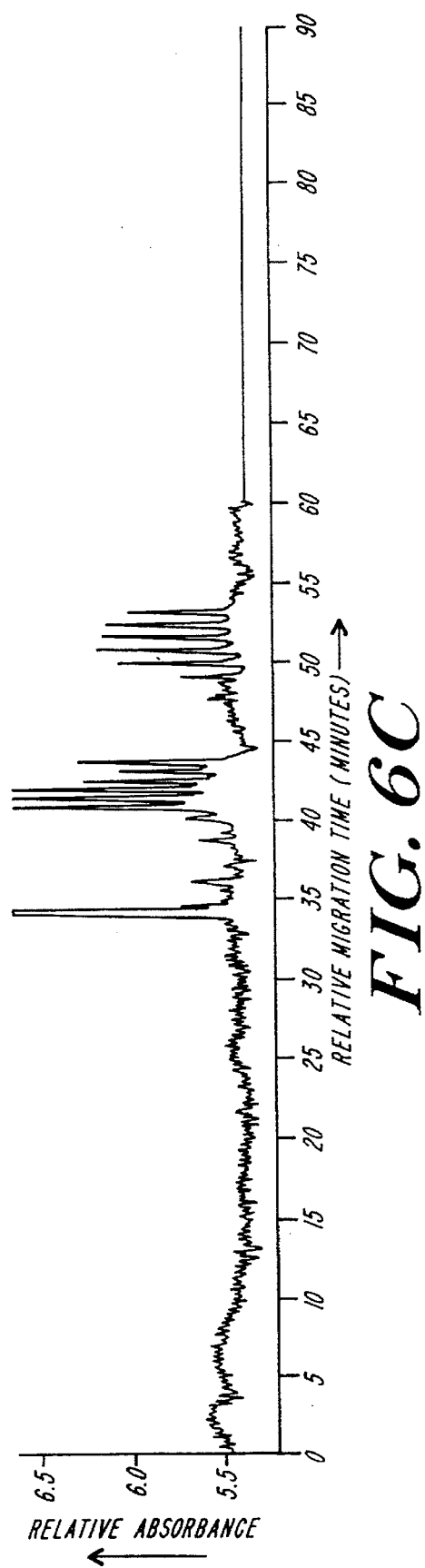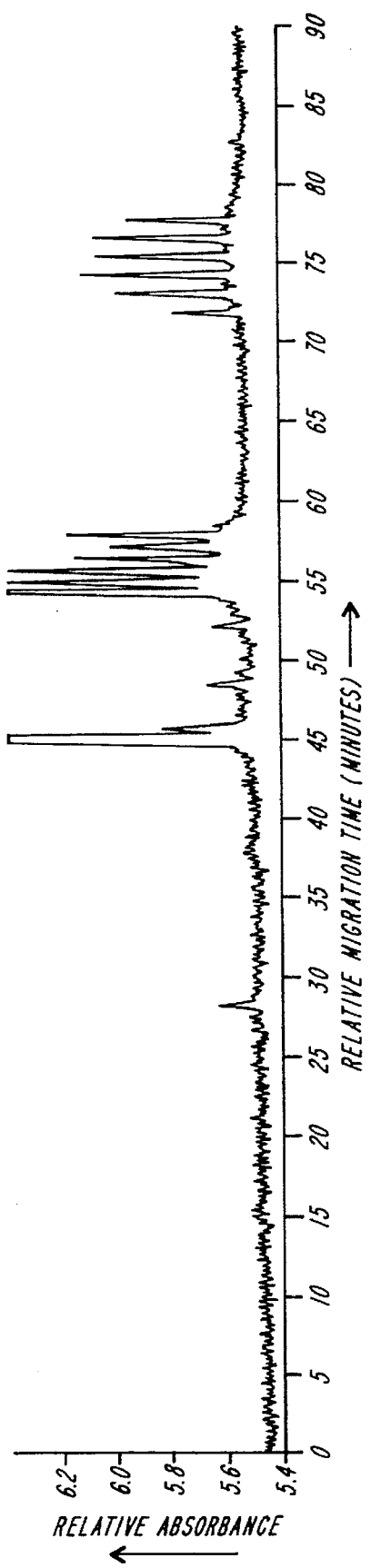

METHOD FOR ANALYZING OLIGONUCLEOTIDE ANALOGS

CROSS-REFERENCE TO RELATED APPLICATION

This patent application is a continuation-in-part of patent application Ser. No. 08/032,856, filed Mar. 16, 1993, entitled ANALYTICAL TECHNIQUE FOR OLIGONUCLEOTIDE ANALOGS, pending which, is a continuation-in-part of patent application Ser. No. 07/991,466 of the same title, filed Dec. 16, 1992, now U.S. Pat. No. 5,420,265.

FIELD OF THE INVENTION

This invention relates to methods for separating mononucleotides and oligonucleotides. More particularly, this invention relates to the separation and characterization of modified and unmodified mononucleotides and oligonucleotides by high performance capillary electrophoresis.

BACKGROUND OF THE INVENTION

Oligonucleotides that are complementary or "antisense" to specific genes or RNA sequences are relatively small, synthetic molecules having an average molecular weight of about 10 kilodaltons (kD). These antisense molecules have had widespread use in the field of selective gene regulation with consequent therapeutic implications. Phosphate backbone modification of such oligonucleotides provides nuclease resistance and greatly enhances the usefulness of these analogs. Such modifications include the substitution of phosphodiester internucleotide linkages with linkages such as methylphosphonates (Murakami et al. (1986) *Biochem.* 24:4041–4046; Agrawal et al. (1987) *Tetrahedron Lett.* 28:3539–3542; Sarin et al. (1988) *Proc. Nat. Acad. Sci.* (USA) 85:7448–7451), phosphorothioates (Burgers et al. *Biochemistry* 18:592–596; Agrawal et al. (1988) *Proc. Natl. Acad. Sci.* (USA) 85:7079–7083; Agrawal et al. (1989) *Nucleosides and Nucleotides* 8:819–823; Agrawal et al. (1989) *Proc. Natl. Acad. Sci.* (USA) 86:7790–7794), and phosphoramidates (Agrawal et al. (1988) *Proc. Natl. Acad. Sci.* (USA) 85:7079–7083; Agrawal et al. (1989) *Nucleosides and Nucleotides* 8:819–823).

Of special interest are phosphorothioate analogs in which one non-bridging oxygen atom has been substituted for a sulfur atom on the phosphate group in one or more internucleotide phosphodiester linkages. This modification is a conservative substitution which increases nuclease resistance without significantly impairing the hybridization of the antisense molecule with target mRNA. As synthesized, these modified oligonucleotides or analogs are usually found as diastereomeric mixtures due to chirality at their phosphorous group. In a context of new drug research, development and manufacturing of such analogs requires that the issues of oligomer length, base composition, base sequence, chemical purity, and stereochemical purity be successfully addressed.

Synthetic oligonucleotides are presently used in most laboratories using molecular biology techniques. As synthesized, these oligonucleotides generally exist as mixtures of truncated oligonucleotides in addition to the desired oligonucleotide. Since the purity and chemical identity of a particular oligonucleotide is crucial to many applications, the ability to characterize and separate synthetic oligonucleotides analogs on a routine basis is important.

The absolute length and the degree of length heterogeneity of prepared oligonucleotides have been assessed by electrophoresis in high resolution denaturing polyacrylamide slab gels (PAGE) (see, e.g., *Current Protocols in Molecular Biology*, Green Publishing and Wiley Interscience, N.Y., 1988) and by capillary gel electrophoresis through cross-linked polyacrylamide (6% T, 5% C) gels (Hjerten (1967) *Chromatogr. Rev.* 9:122–213) containing from 10% to less than 30% (vol.:vol.) formamide (Rocheleau et al. (1992) *Electrophoresis* 13:484–486). Detection of oligonucleotides separated on such gels has been accomplished by autoradiography and laser-induced fluorescence. These methods have not proven suitable for separating modified oligonucleotides. Furthermore, some of these gels, once used, are not easily removable from the capillary. To remedy this problem, gels containing up to 5% acrylamide monomer have been polymerized before filling the capillary (EPO 497 480). Ultrathin slab gels (less than 100 μm in thickness) have also been used for high speed DNA sequencing (Brumley et al. (1991) *Nucleic Acids Res.* 19:4121–4126; Ansorge et al. (1990) *Nucleic Acid Res.* 18:3419–5420). Alternative separation methods include ion exchange chromatography, reversed phase high pressure liquid chromatography (HPLC), and gel high performance capillary electrophoresis (see, e.g., Edge et al. (1981) *Nature* 292:756–762; U.S. Pat. No. 4,865,707).

Oligonucleotides with phosphorothioate linkages are more difficult to resolve than phosphodiester-linked DNA due to the existence of diastereomer isomers ($2^n$, where n=the number of chiral centers, which is equivalent to the number of phosphate groups). In addition, difficulty in resolution may be due to increased hydrophobicity of the former. These molecules, when separated, interact hydrophobically with ion exchange column supports and in many cases co-elute. Thus, they cannot be separated by the above methods in their existing formats.

The separation one phosphorothioate oligonucleotide analogs is problematic for other reasons as well. When phosphorothioate oligonucleotides are assembled using either methoxyphosphoramidite or H-phosphate chemistry, they are in the form of diastereomeric mixtures due to chirality at their phosphorous groups. As a result, although they migrate through polyacrylamide gels and HPLC columns like their corresponding phosphodiester counterparts, phosphorothioate oligonucleotides give broader peaks and run more slowly than phosphodiesters because of their increased hydrophobicity or secondary structure. They are also known to interact with the HPLC column support. In addition, phosphorothioates run into stereochemical problems when separated by reversed phase HPLC. General analytical methods have not been devised for establishing the ratio of the optical isomers at each unsymmetrical substitution phosphorous linkage in an analog having many such sites of local chirality.

HPLC of oligodeoxyribonucleotides containing one or two phosphorothioate internucleotide linkages using a reversed-phase column (RP-HPLC) has been reported (Stec et al. (1985) *J. Chromatogr.* 326:263–280; Agrawal et al. (1990) *Nucleic Acid Res.* 18:5419–5423). However, this method is of limited use because of the small differences in the hydrophobicity of these analogs with increasing chain length (Agrawal et al. (1990) *J. Chromatogr.* 509:396–399).

Separation of oligodeoxyribonucleotide phosphorothioates containing 20 or fewer nucleotides has also been achieved by HPLC on strong and weak anion-exchange (SAX and WAX) columns (Cohen et al. (1993) *J. Chromatogr.* 638:293–301). Unfortunately, oligonucleotide phosphorothioates containing more than 20 nucleotides can not be analyzed by this method because of their strong interaction with the SAX or WAX medium. Thus the separation of oligonucleotide phosphorothioates by this method is limited by its oligonucleotide length dependency.

Length-dependent separation of phosphorothioate analogs by HPLC using a WAX column has also been accomplished by Meletev et al. (*Analyt. Biochem.* (1993) 200:342–346). However, the peaks obtained were broader than those obtained for their phosphodiester counterparts, possibly because of their diastereomeric backbone. Ion-pair HPLC has also been used to analyze oligonucleotide phosphorothioates (Bigelow et al. (1990) *J. Chromatogr.* 533:133–140), but length-dependent separation was not achieved.

Thus, what is needed are better analytical methods of, and substrates for, separating unmodified and modified mononucleotides and oligonucleotides cleanly, rapidly, efficiently, and which are not limited by the size range or modification of the molecules being analyzed. Also, what is needed are better methods of, and substrates for, separating and characterizing oligonucleotides such as those which are partially or totally oxidized.

SUMMARY OF THE INVENTION

A novel substrate and method of its use have been developed for the separation and characterization of unmodified and modified mononucleotides and oligonucleotides differing by as little as a single base or oxidation. Furthermore, this method enables the separation and characterization of oxidized oligonucleotides and/or oxidized mononucleotides from unoxidized or partially oxidized oligonucleotides and/or non-oxidized mononucleotides. Ann advantage to the use of this substrate and method is the relative ease by which samples of less than one nanogram per microliter or lower volumes can be conveniently handled with on-line UV detection. Relative to slab gel electrophoresis and conventional gel high performance capillary electrophoresis/on-line UV operation, this new formulation can be very useful for in process analysis as well as for purity assessment of antisense nucleotides in the pharmaceutical industry.

As used herein, an "oxidized oligonucleotide" is one having phosphodiester internucleotide linkages. A "partially oxidized oligonucleotide" is one which has the oxygen in the nonbridging position substituted for another atom or chemical group at some but not all of its internucleotide linkages. An oligonucleotide which is "unoxidized" is one in which the nonbridging oxygen in every phosphate group is substituted with another atom or chemical group.

The substrate of the invention includes at least 12% (weight:volume) polymer, which, in preferred embodiments is no more than 1% cross-linked, in at least 5M urea and at least 32% (volume:volume) organic solvent. The organic solvent is a chemically sizable liquid at room temperature (from about 19°–25° C.) and has a dielectric constant of at least 20. In one aspect of the invention, the substrate includes from 0 to 16.2% water.

Preferable substrate polymers are polyacrylamide, methyl cellulose and derivatives thereof, and polyvinyl alcohol. In one aspect, the substrate of the invention is acrylamide, and in particular, includes at least 12% T polymerized acrylamide (or polyacrylamide). The term "T" refers to the percent of monomers (mass:volume). In one embodiment, the invention includes a substrate containing 18% T polyacrylamide. In another aspect of the invention, the substrate includes polyacrylamide such as 12% to 20% T polyacrylamide, with from about 13% to 18% T being optimal. In another aspect, the substrate contains linear polyacrylamide. The polymer is non-cross-linked in some aspects of the invention, and in others, contains up to 1% cross-linking.

Preferable organic solvents making up the substrate and having a dielectric constant of at least 20 are methanol, formamide, acetaldehyde, dimethylsulfoxide (DMSO), ethanol, glycol, acetone, 1-propanol, 2-propanol, 1, 2-propanediol, 1, 3-propanediol, and glycerol. In two representative embodiments of the invention, the substrate includes either formamide present at a concentration of about 32% to 74% (volume:volume) or DMSO at a concentration of about 32% to 56% (volume:volume). In yet another embodiment, the substrate includes 14% to 56% (volume:volume) DMSO.

The invention also provides a method of separating unmodified and modified mononucleotides and oligonucleotides using the above-described substrate. This method includes placing the substrate in a high performance capillary, and then contacting the substrate with the mononucleotide and/or oligonucleotides to be separated. An electric field greater than 200 volts/centimeter is applied across the substrate in the capillary, and the separated mononucleotides and/or oligonucleotides are detected. In preferred embodiments of the invention, an electric field of about 400 to 800 volts/cm is applied across the substrate.

Molecules capable of being separated by this method include unmodified mononucleotides, unmodified oligonucleotides, mononucleotide analogs, and oligonucleotide analogs, all having from about 1 to 150 bases.

As used herein, a "mononucleotide analog" or "modified mononucleotide" is a base, including purines and pyrimidines, or modifications thereof, attached to the 1' end of the deoxyribose or ribose sugar, or modifications thereof, which is attached at its 5' position to a phosphate group. Also included as a mononucleotide analog are cyclic mononucleotides.

The term "mononucleotide analog" or "modified mononucleotide" is also meant to encompass 5'-substituted mononucleotide analogs which include a deoxyribose or ribose sugar attached at its 5' position to a chemical group other than the phosphate group found in native nucleotides. Preferable chemical groups include alkyl phosphonates, phosphorothioates, phosphorodithioates, alkyl phosphorothioates, phosphoramidates, phosphate esters, carbonates, phosphate diesters, carbamates, and phosphate triesters. "Mononucleotide analogs" or "modified mononucleotides" also include "3'-substituted mononucleotide analogs" having a deoxyribose or ribose sugar attached at their 3' position to a chemical group other than the hydrogen found in native nucleotides. Also included in the terms "modified mononucleotide" and "mononucleotide analog" are 3',5'-substituted mononucleotides having a sugar which, at both its 3' and 5' positions is attached to a chemical group other than a hydroxyl group (at its 3' position) and other than a phosphate group (at its 5' position). A modified mononucleotide or mononucleotide analog may also be unoxidized, i.e., having a substitution in one nonbridging oxygen as in a phosphorothioate, for example.

The term "oligonucleotide" includes polymers of one or more ribonucleotide and/or deoxyribonucleotide monomers connected together or linked by at least one 5' to 3' internucleotide linkage.

The terms "modified oligonucleotide" and "oligonucleotide analog," as used herein, encompass a molecule of ribonucleotides or deoxyribonucleotides which are covalently linked via at least one synthetic linkage. A "synthetic internucleotide linkage" is a linkage other than a phosphodiester between the 5' end of one nucleotide and the 3' end of another nucleotide in which the 5' internucleotide phosphate has been replaced with any number of chemical groups. Preferable synthetic linkages include alkylphosphonates, phosphorothioates, phosphorodithioates, alkylphosphonothioates, phosphoramidates, phosphate esters, carbamates, carbonates, phosphate triesters, acetamidate, and carboxymethyl esters.

The terms "modified oligonucleotide" and "oligonucleotide analog" also encompass oligonucleotides with a modified base and/or sugar. For example, a 3', 5'-substituted oligonucleotide is a modified oligonucleotide having a sugar which, at both its 3' and 5' positions is attached to a chemical group other than a hydroxyl group (at its 3' position) and other than a phosphate group (at its 5' position). A modified oligonucleotide may also be a capped species. Also encompassed by these terms are unoxidized oligonucleotides or oligomers having a substitution in one nonbridging oxygen per nucleotide in the molecule.

Synthetic oligonucleotides are also oligonucleotide analogs. A "synthetic oligonucleotide" encompasses polymers of 3' to 5'-linked ribonucleosides, 2'-modified ribonucleosides and/or deoxyribonucleosides having only as many nucleosides as are conveniently chemically synthesized (i.e., up to about 80–90). Also encompassed are those oligonucleotides having base or sugar modifications as well as those having nuclease resistance-conferring bulky substituents at their 3' and/or 5' end(s), multiple ribonucleosides and/or deoxyribonucleosides linked via an internucleotide linkage not found in native DNA, i.e., linkages other than phosphodiester bonds, or having modified bases and/or sugars in various other structural modifications not found in vivo without human intervention.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 4A is an electropherogram demonstrating the electrophoretic separation of unoxidized heteropolymers differing in length by one base, using a substrate composed of 12.6% T acrylamide, 7.4M urea, and 40.5% (volume:volume) DMSO by HPCE (800 V/cm, 3 µA) on 10 cm capillaries;

FIG. 4B is an electropherogram demonstrating the electrophoretic separation of oxidized homopolymers of polyadenylic acid differing in length by one base, using a substrate composed of 12.6% T acrylamide, 7.4M urea, and 40.5% (volume:volume) DMSO by HPCE (800 V/cm, 3 µA) on 10 cm capillaries;

FIG. 4C is an electropherogram demonstrating the electrophoretic separation of unoxidized oligonucleotide analogs differing in length by only one base, and oxidized homopolymers of polyadenylic acid differing in length by one base, using a substrate composed of 12.6% T acrylamide, 7.4M urea, and 40.5% (volume:volume) DMSO by HPCE (800 V/cm, 3 µA) on 10 cm capillaries;

FIG. 5A is an electropherogram demonstrating the electrophoretic separation of unoxidized heteropolymers differing in length by one base, using a substrate composed of 11.4% T acrylamide, 5.7M urea, and 48.9% (volume:volume) formamide by HPCE (400 V/cm, 4 µA) on 10 cm capillaries;

FIG. 5B is an electropherogram demonstrating the electrophoretic separation of homopolymers of oxidized polyadenylic acid differing in length by one base, using a substrate composed of 11.4% T acrylamide, 5.7M urea, and 48.9% (volume:volume) formamide by HPCE (400 V/cm, 4 µA) on 10 cm capillaries;

FIG. 5C is an electropherogram demonstrating the electrophoretic separation of unoxidized heteropolymers differing in length by one base and oxidized homopolymers of polyadenylic acid differing in length by one base, using a substrate composed of 11.4% T acrylamide, 5.7M urea, and 48.9% (volume:volume) formamide by HPCE (400 V/cm, 4 µA) on 10 cm capillaries;

FIG. 6C is an electropherogram demonstrating the electrophoretic separation of unoxidized heteropolymers differing in length by one base and oxidized homopolymers of polyadenylic acid differing in length by one base, using a substrate composed of 14.0% T acrylamide, 5M urea, and 42% (volume:volume) DMSO;

FIG. 6D is an electropherogram demonstrating the electrophoretic separation of unoxidized heteropolymers differing in length by one base and oxidized homopolymers of polyadenylic acid differing in length by one base, using a substrate composed of 14.0% T acrylamide, 5M urea, and 56% (volume:volume) DMSO;

DETAILED DESCRIPTION OF THE PREFERRED EMBODIMENTS

Figure 1A:
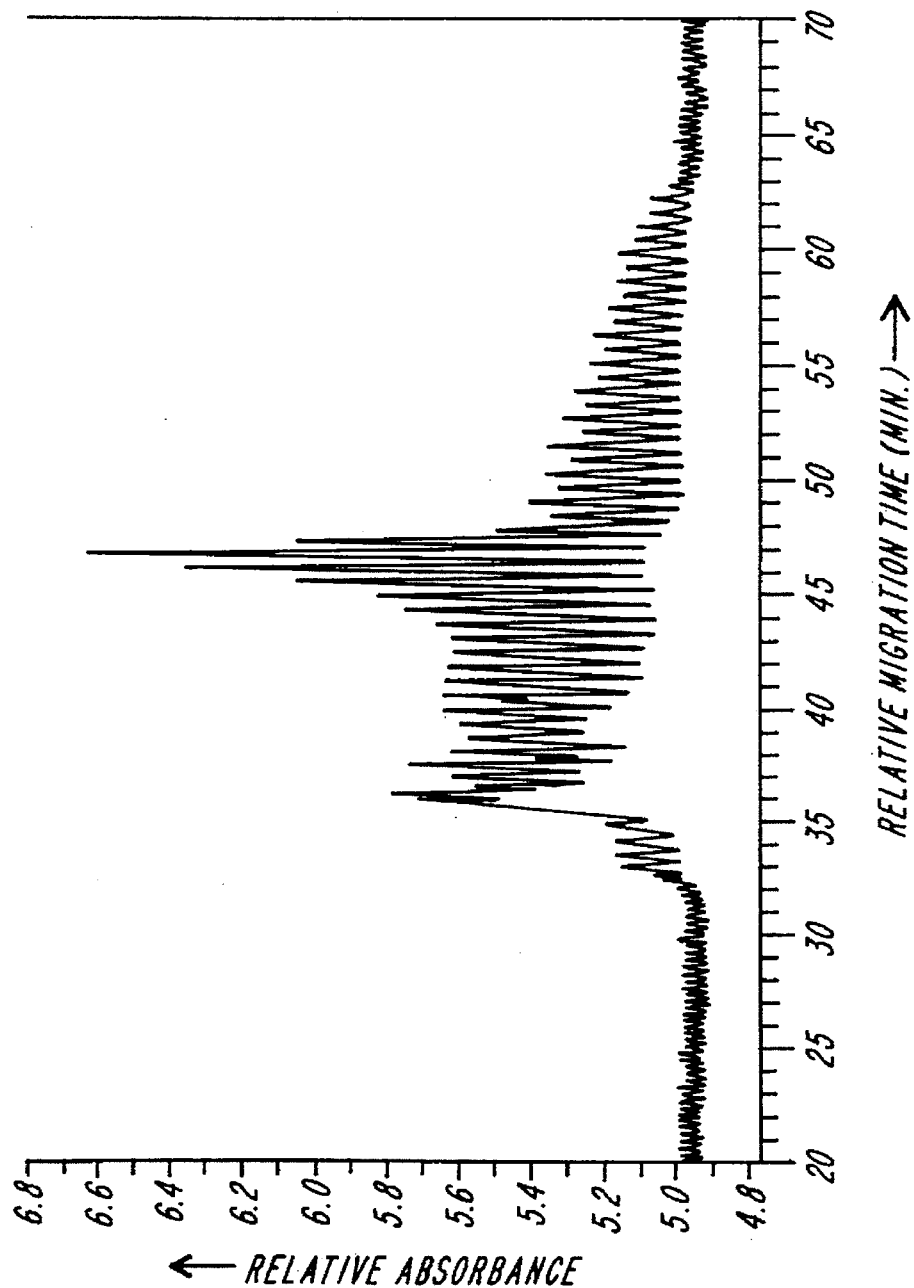
FIG. 1A is an electropherogram demonstrating the separation by HPCE of phosphorothioate failure sequences ranging in length from 1 to 50 bases in length.

This invention provides a novel substrate and methods of using that substrate to separate unmodified and modified mononucleotides and unmodified and modified oligonucleotides which may differ by only one base or oxidation.

High performance capillary gel electrophoresis (HPCE) utilizing the novel substrate of the invention holds a unique position in the field of oligonucleotide separation due to its resolution power, ability to determine purity, speed, and automation. Because of the low current generated (µA) from the narrow bore columns (25 µm to 200 µm, inner diameter), high electric fields (hundreds of volts/cm) without excess Joule heating can be employed, resulting in very rapid, high resolution separations. As an instrumental technique, HPCE is reproducible, amenable to automation, and thus is a powerful alternative tool for antisense analysis.

Results obtained by traditional capillary electrophoresis suggest the application of electric fields lower than 200 V/cm with low ionic strength buffer (not higher than 0.1M Tris-borate-EDTA (TBE)) and low gel concentration in aqueous media for the separation of oligonucleotides. However, it has been discovered that the use of 0.2M TBE buffer and an electric field of at least 200 V/cm, and preferably at least 400 V/cm, gives very high resolution in certain gel substrates for the separation of oligonucleotide analogs.

The substrate contains a polymer such as polyacrylamide, methyl cellulose, polyvinyl alcohol, or derivatives thereof, which may be up to 1% cross-linked but need not be cross-linked at all. It is important that the concentration of polymer in the capillary be 12% or higher to achieve this kind of resolution and efficiency. No concentration gradient of polymer is required, but linear gradients of, for example, from about 12% to 20%, or more preferably, from about 13% to 18% polymer are useful.

The polymer is suspended in a solution containing at least 5M urea. The presence of a high concentration of urea (i.e., at least 5M, and preferably between 5.7 and 8.3M) improves denaturation of the molecules to be separated under the conditions of this method.

The solution also contains at least 32% (volume:volume) organic solvent. Useful organic solvents are chemically stable liquids at about room temperature, and have a dielectric constant of at least 20. Such solvents include, but are not limited to, methanol, formamide, acetaldehyde, DMSO, ethanol, glycol, acetone, 1-propanol, 2-propanol, 1,2-propanediol, 1,3-propanediol, and glycerol, among others. These solvents, along with their chemical formulae and dielectric constants, are listed below in TABLE 1 obtained from *The Merck Index* ((10th Ed.) Windholz et al., eds., (1983) Merck & Co., Inc., Rahway, N.J.).

TABLE 1

| Chemical Formula | Solvent | Dielectric Constant | at °C. |
|---|---|---|---|
| $CH_4O$ | methanol | 33.62 | 20° |
| $CH_3NO$ | formamide | 84.0 | 20° |
| $C_2H_4O$ | acetaldehyde | 21.0 | 10° |
| $C_2H_6OS$ | dimethylsulfoxide | 45.0 | 20° |
| $C_2H_6O$ | ethanol | 24.30 | 25° |
| $C_2H_6O_2$ | glycol | 37.0 | 25° |
| $C_3H_6O$ | acetone | 20.7 | 25° |
| $C_3H_8O$ | 1-propanol | 20.1 | 25° |
| $C_3H_8O$ | 2-propanol | 18.3 | 25° |
| $C_3H_8O_2$ | 1,2-propanediol | 32.0 | 20° |
| $C_3H_8O_2$ | 1,3-propanediol | 35.0 | 20° |
| $C_3H_8O_3$ | glycerol | 42.5 | 25° |

In addition, some substrates of the invention include about 14% to 56% DMSO.

The substrate consisting of the polymer in the urea/organic solvent solution is placed in a capillary or tube before polymerization in preparation for separation and analysis by HPCE. In the case of acrylamide, polymerization may be achieved by adding ammonium persulfate and a free radical catalyst such as N,N,N',N'-tetramethylenediamine (TEMED) to the acrylamide solution. Alternatively, photopolymerization may be used. The substrate solution is then placed into the capillary where it polymerizes. A useful capillary is a microcapillary column (25 to 200 µm inner diameter) made of fused silica, as described in U.S. Pat. Nos. 4,865,706 and 5,112,460, herein incorporated by reference. Of course, other initiators and modes of polymerization may be used depending on the type of polymer present in the substrate.

The sample solution containing the molecules to be analyzed is then applied to the substrate in the capillary. The molecules which can be successfully separated on this substrate include unmodified mononucleotides and oligonucleotides and modified mononucleotides and oligonucleotides (or mononucleotide analogs and oligonucleotide analogs) such as oxidized and unoxidized mononucleotides and oligonucleotides, 3'-substituted mononucleotides and oligonucleotides, 5'-substituted mononucleotides and oligonucleotides, 3',5'-substituted mononucleotides and oligonucleotides, mononucleotides and oligonucleotide analogs having at least one phosphate group replaced with a chemical group such as alkylphosphonates, phosphorothioates, phosphorodithioates, alkylphosphonothioates, phosphoramidates, phosphate esters, carbamates, carbonates, phosphate triesters, acetamidate, and carboxymethyl esters, among others (see, e.g.,. Uhlmann et al. (1990) *Chem. Rev.* 90:543–583).

The preparation of these modified and unmodified mononucleotides and oligonucleotides is well known in the art (reviewed in Agrawal et al. (1992) *Trends in Biotechnol.* 10:152–158). For example, monomeric and oligomeric phosphorothioate analogs can be prepared using methods well known in the field such as methoxyphosphoramidite (see, e.g., Agrawal et al. (1988) *Proc. Natl. Acad. Sci.* (USA) 85:7079–7083) or H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used.

The products of any of these syntheses may include failure sequences as well as the desired oligonucleotide sequence. The failure sequences have at least one less base than the desired oligonucleotide, but the position of the missing base is unknown without subsequent sequencing analysis.

In order to separate the failure sequences from the desired oligonucleotides so produced, or in order to distinguish, characterize, and isolate different desired mononucleotides and/or oligonucleotide species from each other, the molecules to be examined are analyzed by HPCE using a capillary electrophoresis apparatus. Such an instrument is well known in the field (see, e.g., Cohen et al. (1988) *Proc. Natl. Acad. Sci.* (USA) 85:9660–9663). The sample is electrophoretically injected into the column by dipping the cathodic end of the capillary into the sample solution and applying a field of 400 V/cm for 1 to 3 sec. The sample is then run through the gel, and the separated analogs detected by UV, infrared, fluorescence, laser-induced fluorescence or other external monitoring methods.

Figure 1B:
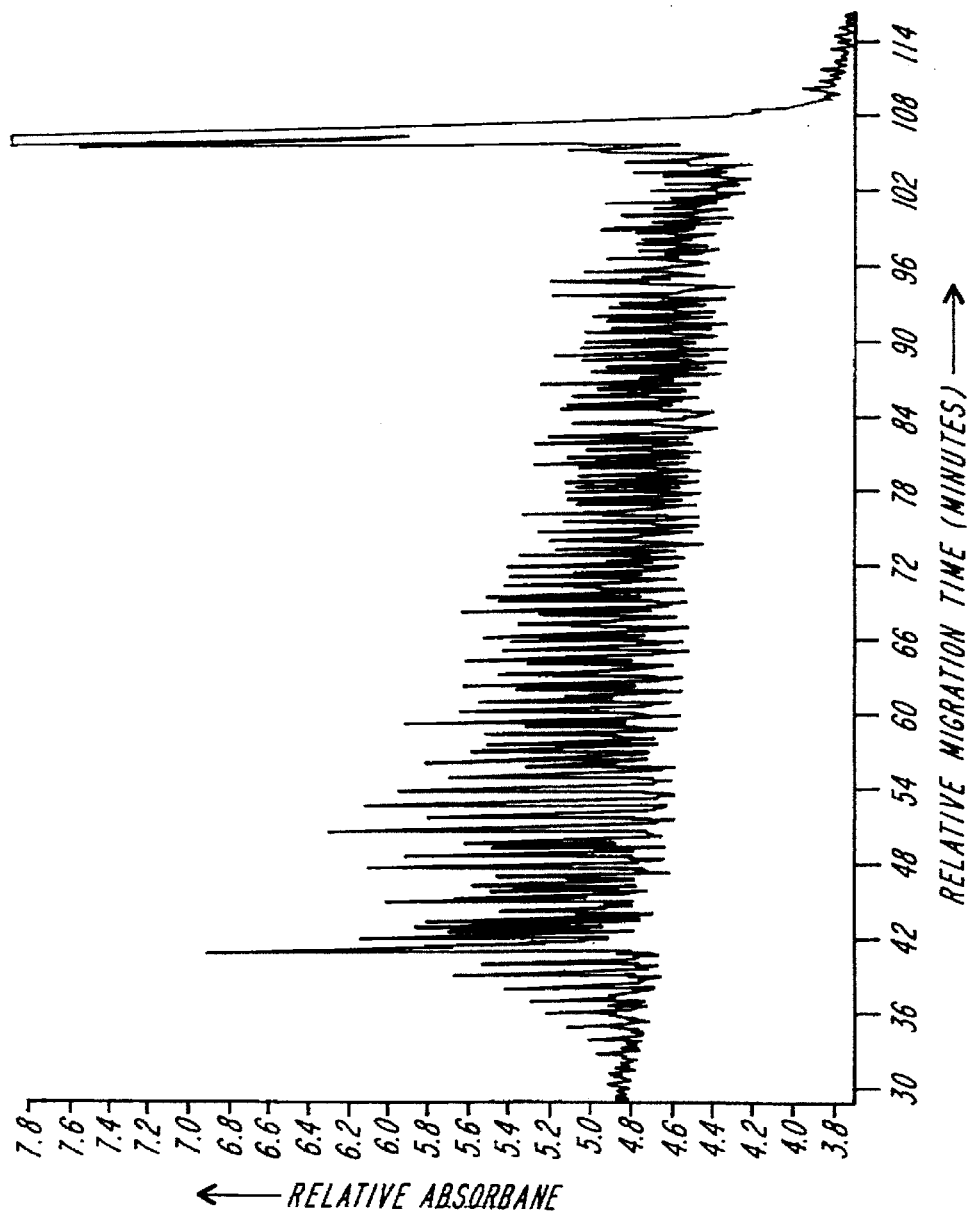
FIG. 1B is an electropherogram demonstrating the electrophoretic separation by HPCE of phosphorothioate failure sequences ranging in length from 1 to 75 bases in length.
Figure 8:
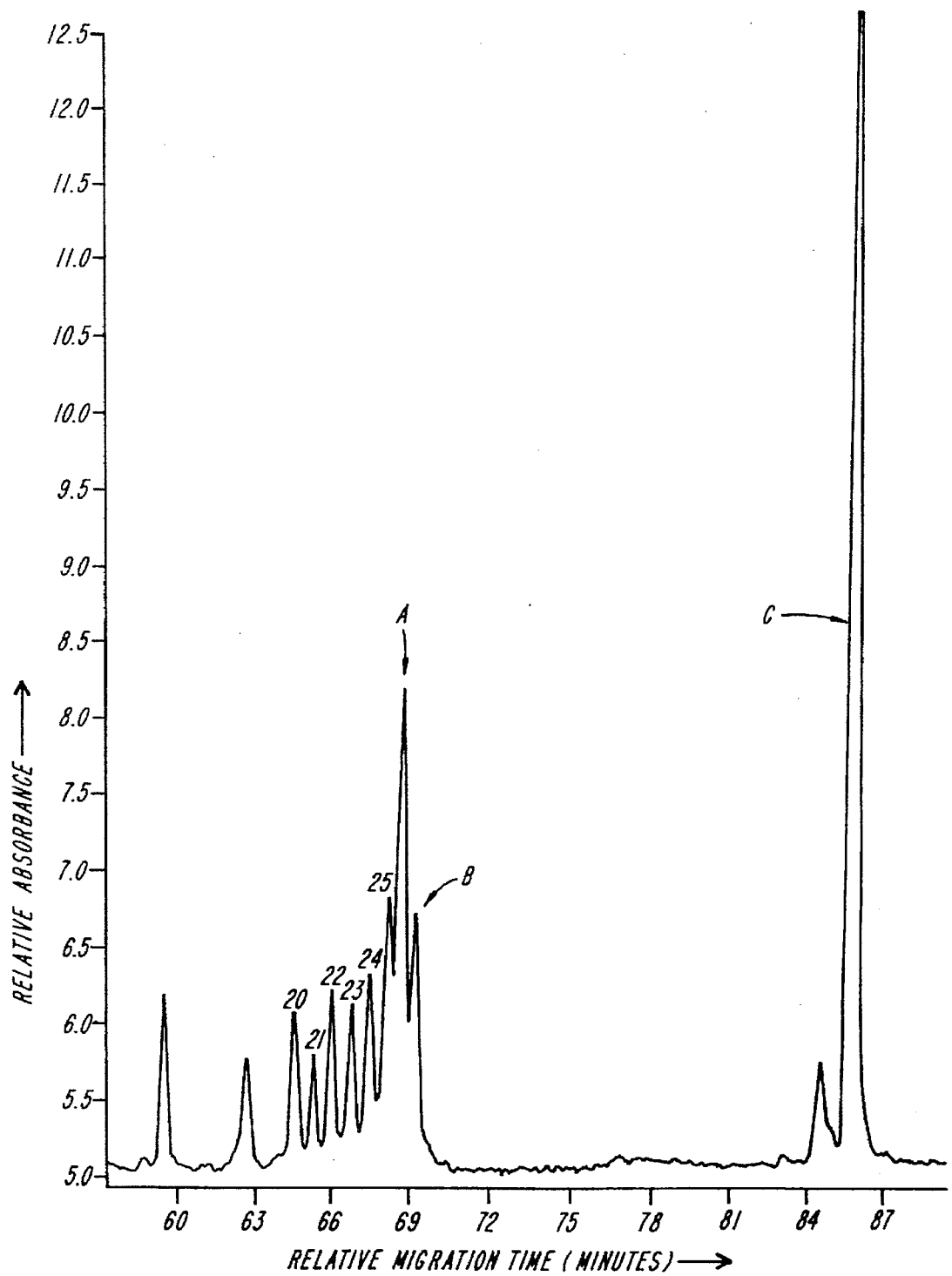
FIG. 8 is an electropherogram demonstrating the electrophoretic separation of unoxidized oligonucleotide analogs 20 to 25 bases in length (SEQ ID NOS:3-7), an oligonucleotide analog (SEQ ID NO:3) with one oxidation, an oligonucleotide analog (SEQ ID NO:3) with two oxidations, and an oligonucleotide analog (SEQ ID NO:3) with twenty-four oxidations, using a substrate composed of 14% T acrylamide, 52% (volume:volume) DMSO, 5M urea, and 200 mM TBE by HPCE (400 V/cm, 5 µA) on a 9 cm capillary.

As demonstrated by the electropherograms shown in FIGS. 1A and 1B, this method enables the separation of oligonucleotide analogs differing in length by only one base. In addition, this method enables the separation of oligonucleotides differing in their state of oxidation by only one oxidized nonbridging group as demonstrated in FIG. 8.

The following examples illustrate the preferred mode of making and practicing the present invention, but are not meant to limit the scope of the invention.

EXAMPLES

1. HPCE Apparatus

The high performance capillary electrophoresis apparatus with UV detection and the preparation of substrate-filled capillary for the separation of DNA molecules are essentially the same as described in Cohen et al. (*Proc. Natl. Acad. Sci.* (USA) (1988) 85:9660–9663) and Heiger et al. (*J. Chromatogr.* (1990) 516:33–48), herein incorporated by reference. A 30 kV, 500 µA direct current high voltage power supply (Model ER/DM; Glassman, Whitehouse Station, N.J.) is used to generate the potential across: the capillary.

2. Preparation of Substrate-Filled Capillaries

Fused-silica capillary tubing (Polymicro Technologies, Phoenix, Ariz.) with inner diameter of 75 µm, outer diameter of 375 µm, effective length of 20 cm, and total length of 30 cm, is treated with (methylacryloxypropyl)trimethoxysilane (Petrarch Systems, Bristol, Pa.) and then filled with degassed 13 to 18% T polymerizing acrylamide in aqueous or organic solution in 0.2M TBE buffer (0.2M Tris borate, 4 mM EDTA), pH 8.3, with 7M to 8.3M urea. Alternatively, capillaries are filled with a degassed 0.2M TBE buffer solution of 11.4%, 13%, or 18% T acrylamide, in 32% to 74% (volume:volume) formamide, 5.7M urea; or 14% T acrylamide in 14% to 56% (volume:volume) DMSO, 5M urea; or 12.6% to 14% T acrylamide in 5 to 7.4M urea and 40.5% (volume:volume) DMSO. Polymerization is achieved by adding ammonium persulfate solution and TEMED. To remove impurities from the polyacrylamide, the capillary column is pre-electrolyzed at 6 kV for 30 to 60 minutes. During electrophoresis, the capillary is maintained at room temperature. Ultra-pure Trizma base, urea, acrylamide, and EDTA are purchased from Schwartz/Mann Biotech (Cleveland, Ohio). TEMED and ammonium persulfate are purchased from Bio-Rad (Richmond, Calif.).

3. Preparation of Oligonucleotides

The oligonucleotide phosphorothioate 25 mer 5'-CGTATAGCCTGATGTCATAGCCGAT-3' (SEQ ID NO:1), 24-mer 5'-GACTCGAGGTCTGCTAACCTAGAT-3' (SEQ ID NO:2), 25 mer 5'-CTCTCGCACCCATCTCTCTCCTTCT-3' (SEQ ID NO:3), 24 mer 5'-TCTCGCACCCATCTCTCTCCTTCT-3' (SEQ ID NO:4), 23 mer 5'-CTCGCACCCATCTCTCTCCTTCT-3' (SEQ ID NO:5), 22 mer 5'-TCGCACCCATCTCTCTCCTTCT-3' (SEQ ID NO:6), 21 mer 5'-CGC-ACCCATCTCTCTCCTTCT-3' (SEQ ID NO:7), 20 mer 5'-CGCACC-CATCTCTCTCCTTCT-3' (SEQ ID NO:8), poly d[T] analogs ranging in length from 19 to 24 bases, and the failure sequences from the syntheses of various oligomers having a length of up to 150 bases (base sequences unknown) are synthesized using the procedure of Beaucage et al. (U.S. Pat. No. 5,003,097), herein incorporated by reference. Briefly, oligodeoxyribonucleotides are synthesized on an automated synthesizer (Model 8700, Milligen/Biosearch, Bedford, Mass.). Both normal phosphodiester oligodeoxyribonucleotides and their phosphorothioate analogs are assembled using H-phosphonate chemistry (Andrus et al. (1988) *Tetrahedron Lett.* 29:61; Gregg et al. (1987) *Tetrahedron Lett.* 27:4051). Synthesis is carried out on a 10-µmol scale, and after the chain elongation cycles the controlled pore glass support-bound oligonucleoside. H-phosphonate in treated either with 0.2M sulfur in carbon disulfide:pyridine: triethylamine (12:12:1, volume:volume) to generate phosphorothioate internucleotide linkages. Deprotection of oligodeoxyribonucleotide in carried out with concentrated ammonia at 55° C. for 8 hours. Deprotected oligodeoxyribonucleotides are then resuspended in distilled water.

4. Separation of Oligonucleotides

Samples are electrophoretically injected into the column by dipping the cathodic end of the capillary into the sample solution and applying a voltage of 400 V/cm for 2 seconds. Separation is achieved at a typical applied field of from 400 to 800 V/cm. Each column is used for multiple injections. Periodically, a short section of the capillary at the injection end is trimmed.

Figure 2:
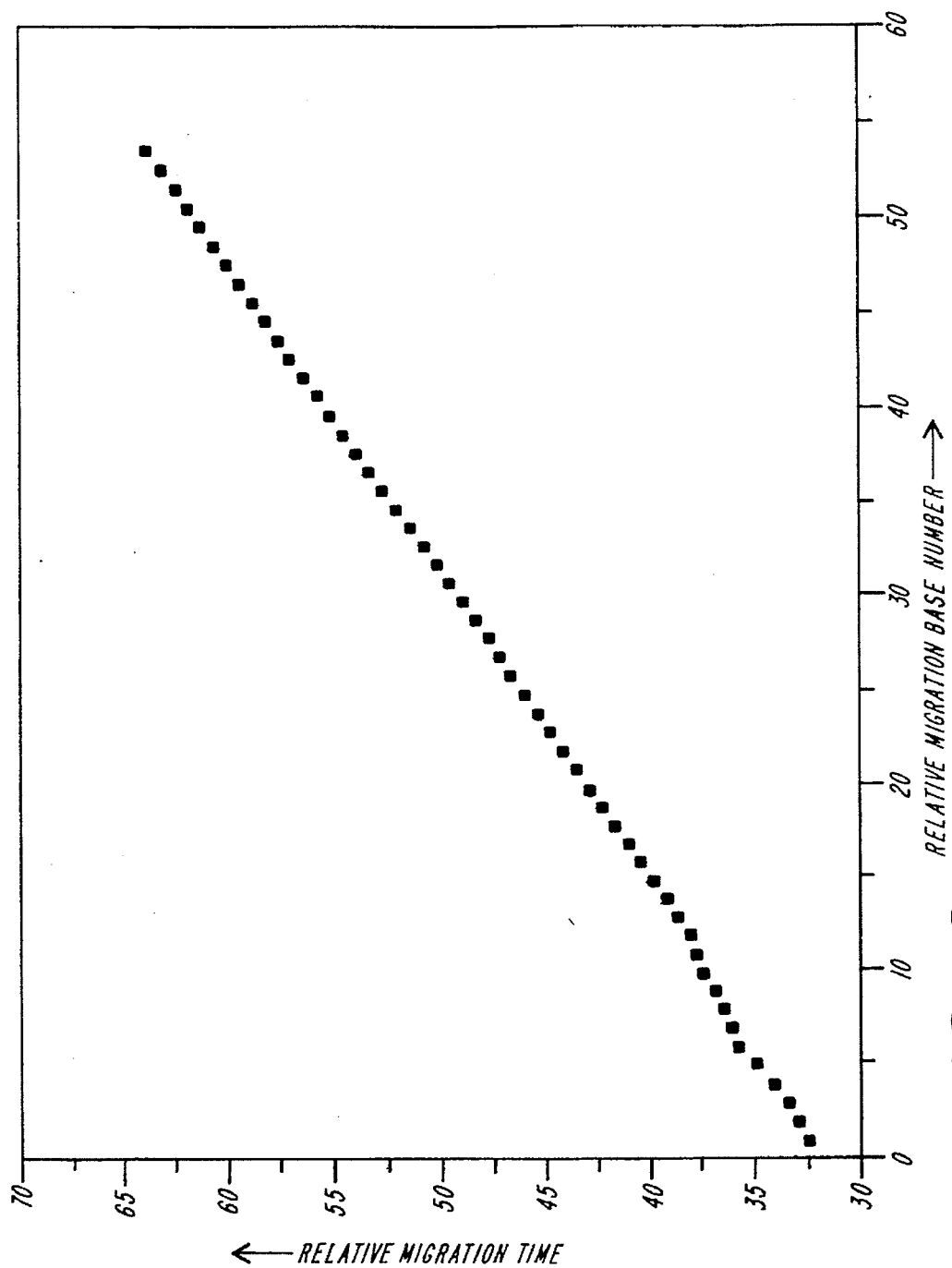
FIG. 2 is a calibration plot of migration time of the analogs separated in FIG. 1 versus oligomer length in the analog.

The failure sequence sample (containing oligonucleotides varying in length from 1 to 50 bases, from 1 to 75 bases, and from 1 to 150 bases) is suspended in water with final concentration 500 ng/µl. Each of these samples is separated on a capillary containing 15% T acrylamide. The column is developed with 60% (volume:volume) formamide, 0.2M TBE buffer, 8.3M urea, pH 8.3. Electrophoresis is conducted under an applied electric field of 400 volts/cm and a current of 5 µA over a 20 cm migration distance. The results from the 1 to 50 and 1 to 75 base samples are shown in FIGS. 1A and 1B. When migration time is examined with respect to fragment length, a linear relationship ($r^2=0.9999$) is observed (FIG. 2). This linear behavior of the phosphorothioate analogs is indicative of the lack of peak compression, and of migration according to molecular weight or size, each being important elements of successful oligonucleotide separation.

Figure 3:
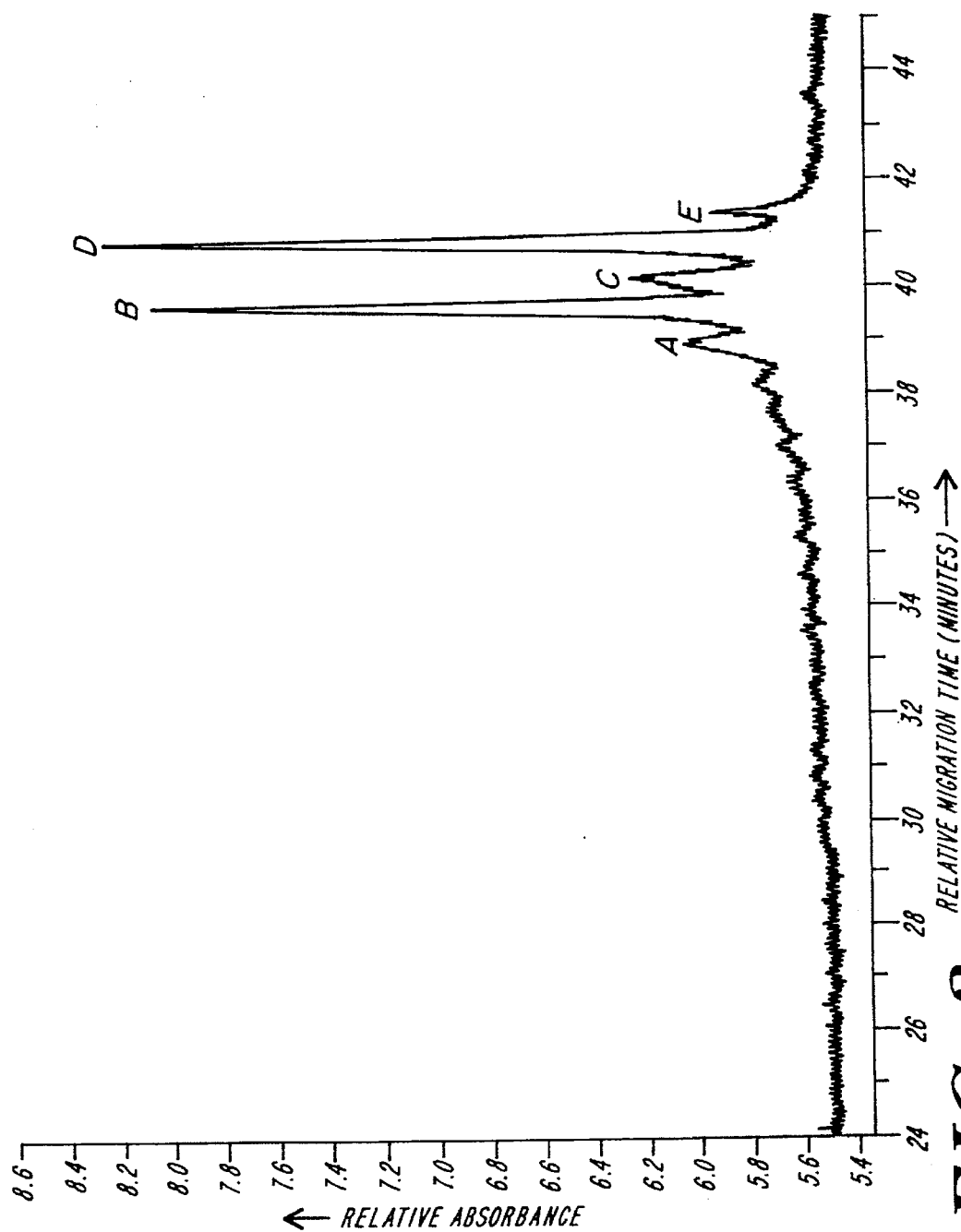
FIG. 3 is an electropherogram demonstrating the electrophoretic separation of a mixture of 25 mer analog (SEQ ID NO:1), 24 mer analog (SEQ ID NO:2), and failure sequences resulting from the syntheses of these oligonucleotide analogs. Peak A represents a putative 23 mer failure sequence from 24 mer (SEQ ID NO:2) synthesis; peak B represents the 24 mer analog (SEQ ID NO:2); peak C represents the putative 24 mer failure sequence from 25 mer analog (SEQ ID NO:1) synthesis; peak D represents a 25 mer analog (SEQ ID NO:1); and peak E is unknown;.

A sample containing a mixture of the 24 mer (SEQ ID NO:2) and the 25 mer (SEQ ID NO:1) phosphorothioate analogs (having different sequences but the same length) is suspended in water to final concentration 400 ng/ml. The sample is run on a capillary containing 13% T, 0% C, 7M urea, 0.2M TBE, pH 8.3. (The term "c" refers to a fraction: the amount of crosslinked polymer over the total monomer and cross-linked monomer). Electrophoresis is conducted under an electric field of 400 volts/cm and a current of 12 µA over a 20 cm migration distance. The results of this separation are shown in FIG. 3. The time window between elution of the 24 mer (SEQ ID NO:2) and elution of the 25 mer (SEQ ID NO:1) is large enough to accommodate an additional peak. This peak is presumed to be a failure sequence of the synthesized 25 mer and is therefore a 24 mer since this peak is migrating directly after the 25 mer under denaturing conditions. Thus, the two 24 mers may be separated due to the difference in their base sequences.

Figure 7A:
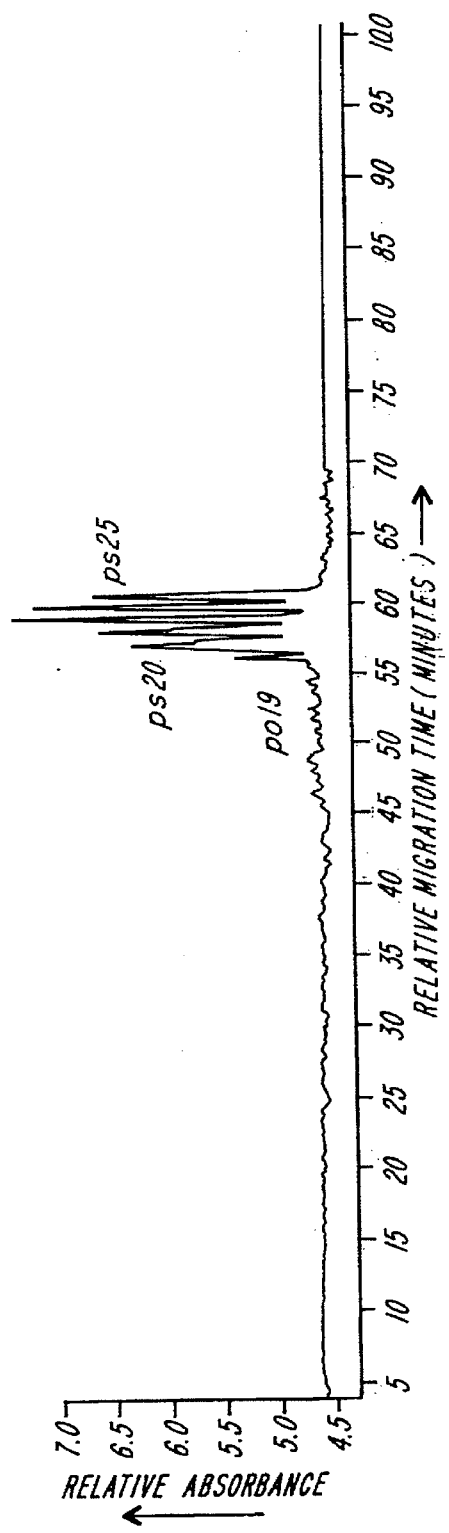
FIG. 7A is an electropherogram demonstrating the electrophoretic separation of unoxidized oligonucleotide analogs 20 to 25 bases in length (SEQ ID NOS 3–8) and homopolymers of polyadenylic acid 19 to 24 bases in length using a substrate composed of 11.4% T acrylamide, 32% (volume:volume) formamide, 7M urea, and 20% water.
Figure 7B:
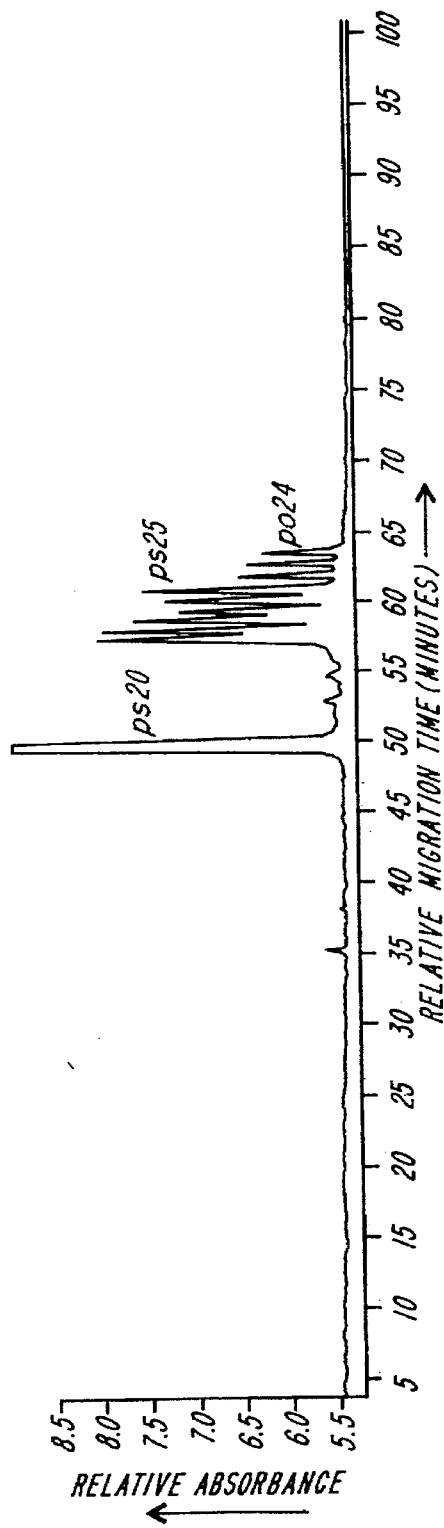
FIG. 7B is an electropherogram demonstrating the electrophoretic separation of unoxidized oligonucleotide analogs 20 to 25 bases in length (SEQ ID NOS 3–8) and homopolymers of polyadenylic acid 19 to 24 bases in length using a substrate composed of 11.4% acrylamide, in 48.9% (volume:volume) formamide, 5.7M urea.
Figure 7C:
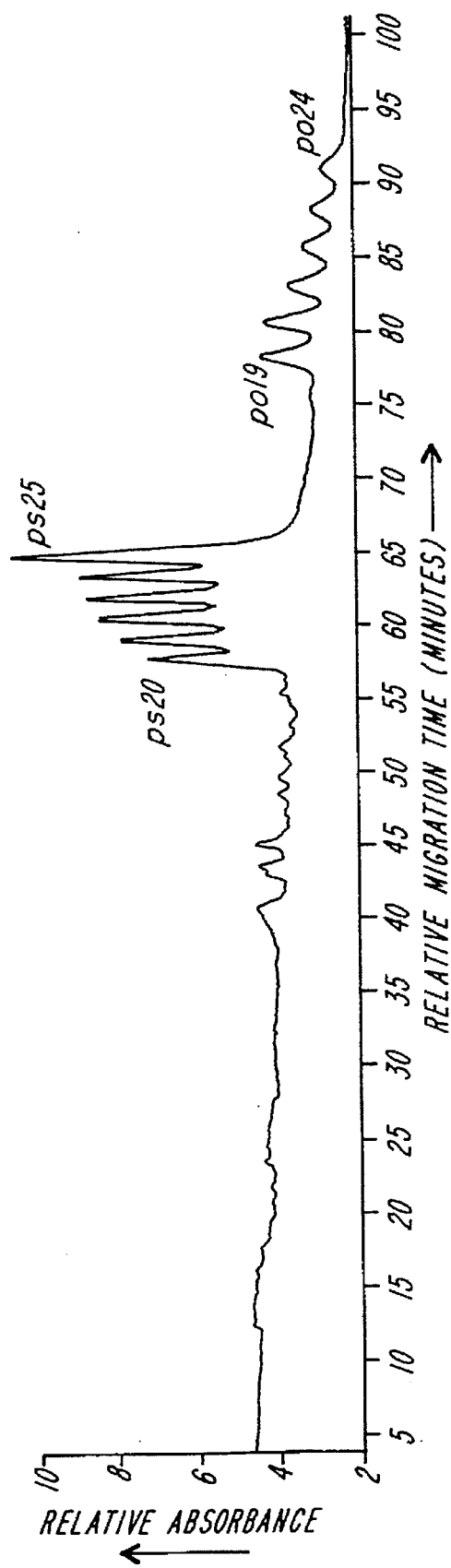
FIG. 7C is an electropherogram demonstrating the electrophoretic separation of unoxidized oligonucleotide analogs 20 to 25 bases in length (SEQ ID NOS 3-8) and homopolymers of polyadenylic acid 19 to 24 bases in length using a substrate composed of 11.4% acrylamide, in 74% (volume:volume) formamide, 5M urea, and 0% water.

In other tests, heteropolymers of unoxidized phosphorothioate oligonucleotide 20–25 mer analogs (SEQ ID NOS:

8, 7, 6, 5, 4, and 3), oxidized homopolymers of polyadenylic acid 19–24 bases in length, and mixtures thereof, are resolved on 10 cm 12.6% T acrylamide capillaries containing 40.5% (volume:volume) DMSO and 7.4M urea at 800 V/cm, 3 μA (FIGS. 4A–4C), on 10 cm 14% T acrylamide capillaries containing 14% to 56% DMSO and 5.0 urea at 800 V/cm, or on 10 cm 11.4% T acrylamide capillaries containing 74% (volume:volume) formamide and 5.7M urea at 400 V/cm, 4 μA (FIG. 7C).

Figure 6A:
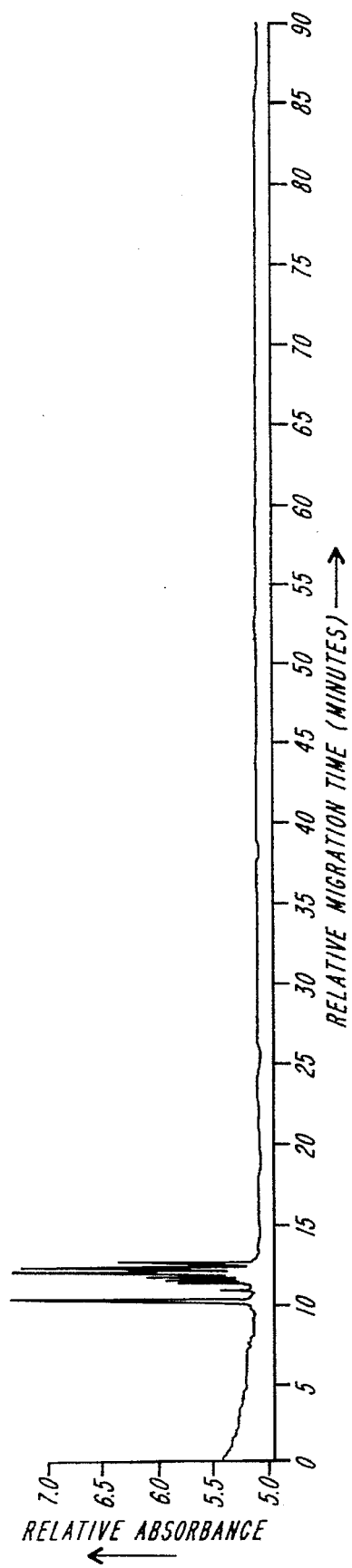
FIG. 6A is an electropherogram demonstrating the electrophoretic separation of unoxidized heteropolymers differing in length by one base and oxidized homopolymers of polyadenylic acid differing in length by one base, using a substrate composed of 14.0% T acrylamide, 5M urea, and 14% (volume:volume) DMSO.
Figure 6B:
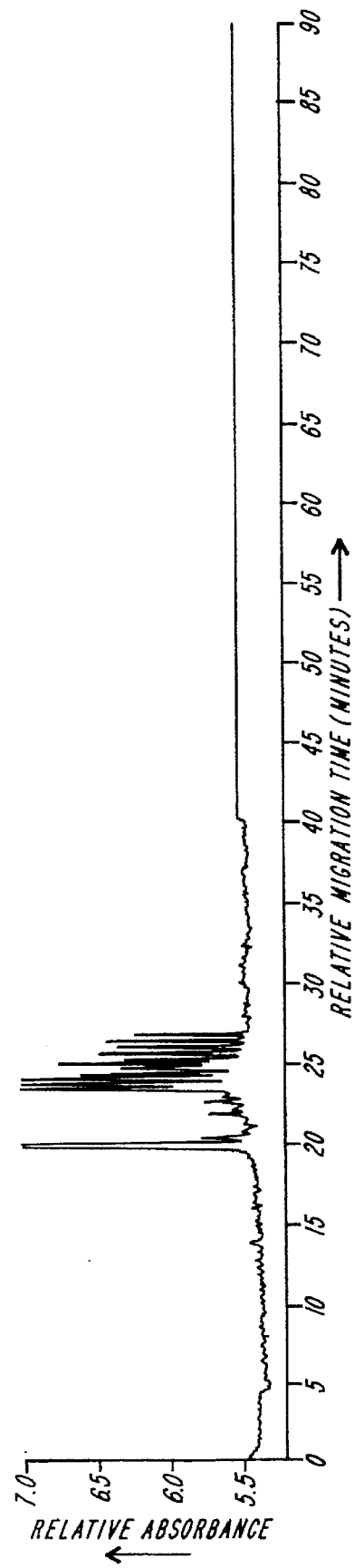
FIG. 6B is an electropherogram demonstrating the electrophoretic separation of unoxidized heteropolymers differing in length by one base and oxidized homopolymers of polyadenylic acid differing in length by one base, using a substrate composed of 14.0% T acrylamide, 5M urea, and 28% (volume:volume) DMSO.

The results show that a substrate containing 40.5% (volume:volume) DMSO and 16.2% water (FIG. 4C) enables the separation of a mixture of completely unoxidized oligonucleotides (e.g., phosphorothioates) differing in length by only 1 base and completely oxidized oligonucleotides (e.g., phosphodiesters) differing in length by only one base, in contrast to a substrate wherein DMSO is substituted for formamide (FIG. 5C). Substrates containing 28% or lower concentration of DMSO are comparable in the separation abilities to that of 48.9% or lower formamide-containing substrates (FIG. 5C). In addition, a substrate containing 74% formamide, 5 to 5.7M urea, and 0% water, is found to separate a mixture of oxidized and unoxidized oligonucleotide analogs differing in length by only one base (FIG. 7C). These results are comparable to the results shown in FIGS. 6C and 6D wherein the substrate contains 42% and 56% (volume:volume), respectively, DMSO.

Thus, the results demonstrate that by increasing organic solvent concentration, improved separation of oligonucleotides differing in length by only one base and by oxidation state can be obtained. Furthermore, substrates containing 14% T acrylamide, 52% (volume:volume) DMSO, 5M urea, and 200 mM TBE can separate unoxidized phosphorothioate heteropolymers 20 to 25 bases in length (SEQ ID NOS:3–8) from each other and from a heteropolymeric analog 25 bases in length (SEQ ID NO:3) having one or two oxidations (see FIG. 8, peaks A and B, respectively; peak C is a 25 mer with 24 oxidations).

5. Detection Method

Oligonucleotides are monitored by UV detection at wavelength 270 nm using a Spectra-100 spectrophotometer (Spectra Physics, San Jose, Calif.). The data are stored on an Ace IBM compatible PC computer via an analog to digital (A/D) converter (Model 970, Nelson Analytical, Cupertino, Calif.).

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. A method of separating modified mononucleotides and/or modified oligonucleotides, comprising the steps of:
    (a) providing, in a capillary, a substrate comprising at least 12% (weight:volume) of a polymer suitable for use in high performance capillary electrophoresis, at least 5M urea and at least 32% (volume:volume) organic solvent, wherein the organic solvent is a chemically stable liquid at room temperature and has a dielectric constant of at least 20;
    (b) contacting the substrate with the mononucleotides and/or oligonucleotides to be separated;
    (c) applying an electric field greater than 200 volts/cm across the substrate in the capillary to separate the mononucleotides and/or oligonucleotides; and
    (d) detecting the separated mononucleotides and/or oligonucleotides.

2. The method of claim 1, wherein the substrate further comprises up to 16.2% (volume:volume) water.

3. The method of claim 1, wherein the polymer is selected from the group consisting of polyacrylamide, methylcellulose, and polyvinyl alcohol.

4. The method of claim 3, wherein the polymer is polyacrylamide.

5. The method of claim 4, wherein the polyacrylamide comprises from about 12% to 20% T acrylamide.

6. The method of claim 5, wherein the polyacrylamide comprises about 18% T acrylamide.

7. The method of claim 4, wherein the substrate comprises polyacrylamide formed in a linear gradient of from about 12% to 18% T acrylamide.

8. The method of claim 1, wherein the substrate comprises a non-cross-linked polymer.

9. The method of claim 1, wherein the substrate comprises a polymer which is up to about 1% cross-linked.

10. The method of claim 1, wherein the substrate comprises 5M to 8.3M urea.

11. The method of claim 1, wherein the organic solvent is selected from the group consisting of methanol, formamide, acetaldehyde, ethanol, dimethylsulfoxide, glycol, acetone, 1-propanol, 2-propanol, glycerol, 1, 2-propanediol, and, 1, 3-propanediol.

12. The method of claim 11, wherein the organic solvent is formamide.

13. The method of claim 12, wherein the substrate comprises about 32% to 74% (volume:volume) formamide.

14. The method of claim 11, wherein the organic solvent is dimethylsulfoxide.

15. The method of claim 14, wherein the substrate comprises about 32% to 52% (volume:volume) dimethylsulfoxide.

16. The method of claim 1 wherein the contacting step (b) comprises contacting the substrate with a modified mononucleotide selected from the group consisting of a 3'-substituted mononucleotide analog, a 5'-substituted mononucleotide analog, and a 3',5'-substituted mononucleotide analog.

17. The method of claim 16, wherein the mononucleotide analog comprises a 5'-linked chemical structure selected from the group consisting of an alkylphosphonate, a phosphorothioate, a phosphorodithioate, an alkylphosphonothioate, a phosphoramidate, a phosphate ester, a carbamate, a carbonate, a phosphate triester, an acetamidate, and a carboxymethyl ester.

18. The method of claim 1 wherein the contacting step (b) comprises contacting the substrate with a modified oligonucleotide having at least one synthetic internucleotide linkage.

19. The method of claim 18, wherein the synthetic internucleotide linkage is selected from the group consisting of an alkylphosphonate, a phosphorothioate, a phosphorodithioate, an alkylphosphonothioate, a phosphoramidate, a phosphate ester, a carbamate, a carbonate, a phosphate triester, an acetamidate, and a carboxymethyl ester.

20. The method of claim 1, wherein the contacting step (b) comprises contacting the substrate with a modified mononucleotide having a 5'-phosphorothioate substitution and a modified oligonucleotide having at least one phosphorothioate internucleotide linkage.

21. The method of claim 1 wherein the contacting step (b) comprises contacting the substrate with a modified oligonucleotide having at least one unoxidized substitution at a nonbridging oxygen.

22. The method of claim 1 wherein the contacting step (b) comprises contacting the substrate with mononucleotides and/or oligonucleotides having from 1 to 150 bases.

23. The method of claim 22 wherein the contacting step (b) comprises contacting the substrate with mononucleotides and oligonucleotides having from 1 to 50 bases.

24. The method of claim 1 wherein the applying step (c) comprises applying an electric field of about 400 volts/cm across the substrate.

25. The method of claim 1 wherein the applying step (c) comprises applying an electric field of about 800 volts/cm across the substrate.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:1:

CGTATAGCCT GATGTCATAG CCGAT      25

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:2:

GACTCGAGGT CTGCTAACCT AGAT      24

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single (D) TOPOLOGY: linear (ii) MOLECULE TYPE: cDNA (iii) HYPOTHETICAL: NO (xi) SEQUENCE DESCRIPTION: SEQ ID NO:3:

CTCTCGCACC CATCTCTCTC CTTCT                                                                                      25

(2) INFORMATION FOR SEQ ID NO:4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO:4:

TCTCGCACCC ATCTCTCTCC TTCT                                                                                       24

(2) INFORMATION FOR SEQ ID NO:5:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO:5:

CTCGCACCCA TCTCTCTCCT TCT                                                                                        23

(2) INFORMATION FOR SEQ ID NO:6:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO:6:

TCGCACCCAT CTCTCTCCTT CT                                                                                         22

(2) INFORMATION FOR SEQ ID NO:7:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO:7:

CGCACCCATC TCTCTCCTTC T                                                                                          21

(2) INFORMATION FOR SEQ ID NO:8:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (xi) SEQUENCE DESCRIPTION: SEQ ID NO:8:

GCACCCATCT CTCTCCTTCT                                                   20